US007015202B2

(12) United States Patent
Suzuki et al.

(10) Patent No.: US 7,015,202 B2
(45) Date of Patent: Mar. 21, 2006

(54) USE OF GLYCYRRHIZIN AND ITS DERIVATIVES AS MCP-1 PRODUCTION INHIBITORS

(75) Inventors: Fujio Suzuki, Galveston, TX (US); Makiko Kobayashi, Galveston, TX (US); Tokuichiro Utsunomiya, Yamato (JP); Hiroatsu Matsumoto, Zama (JP); Midori Takeda, Tokyo (JP); Shigemi Iwata, Yokohama (JP)

(73) Assignee: Minophagen Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/694,616

(22) Filed: Oct. 23, 2003

(65) Prior Publication Data

US 2004/0138171 A1    Jul. 15, 2004

Related U.S. Application Data

(60) Provisional application No. 60/422,338, filed on Oct. 29, 2002.

(51) Int. Cl.
*A61K 31/70* (2006.01)
*A61K 31/56* (2006.01)

(52) U.S. Cl. .................................. 514/26; 514/169
(58) Field of Classification Search .................. 514/26, 514/169
See application file for complete search history.

(56) References Cited

U.S. PATENT DOCUMENTS

2002/0091158 A1   7/2002   Flore

FOREIGN PATENT DOCUMENTS

| EP | 0 255 420 | 7/1987 |
| EP | 0 687 465 | 5/1994 |
| WO | WO02/072084 | 9/2002 |

OTHER PUBLICATIONS

Takei et al., "Glycyrrhizin (GR) Inhibits the Spontaneous Production of Monocytes Chemoattractant Protein-1 (MCP-1) by Peripheral Blood Mononuclear Cells (PBMC) Derived from Patients with AIDS," Abstract T-14, ASM 101st General Meeting, May 22, 2001.
Suzuki et al., "Glycyrrhizin Inhibits the Production of Monocyte Chemoattractant Protein 1 (MCP-1) in Cultures of T Cells and Macrophages," Abstract 327, *Journal of Leukocyte Biology*, Supplement 2001.
Pollard et al., "Glycyrrhizin Inhibits the Production of Monocyte Chemoattractant Protein 1 (MCP-1) in Cultures of Healthy Peripheral Blood Lymphocytes (PBL) Stimulated by IL-10," Abstract 108.4, *Chemokines and Receptors*, p. A1091, date unknown.
Takei et al., "Glycyrrhizin Inhibits the Production of Monocyte Chemoattractant Protein 1 (MCP-1) in Cultures of Healthy Peripheral Blood T Cells Stimulated with IL-1β," Abstract E-28, ASM 102nd General Meeting, May 21, 2002.
Utsunomiya et al., "Effects of Glycyrrhizin, an Active Componenet of Licorice Roots, on *Candida albicans* Infection in Thermally Injured Mice," *Clin Exp Immunol.*, vol. 116, pp. 291-298, 1999.
Utsunomiya et al., "Glycyrrhizin Improves the Resistance of MAIDS Mice to Opportunistic Infection of *Candida albicans*, Through the Modulation of MAIDS-Associated Type 2 T Cell Responses," *Clinical Immunology*, vol. 95, pp. 145-155, 2000.
Sekizawa et al., "Glycyrrhizin Increases the Survival of Mice With Herpes Simplex Encephalitis," *Acta Virologica*, vol. 45, pp. 51-54, 2001.
Utsunomiya et al., "Glycyrrhizin (20β-carboxy-11-oxo-30-norolean-12-en-3β-yl-2-O-β-D-glucopyranuronosyl-α-D-glucopyranosiduronic acid) Improves the Resistance of Thermally Injured Mice to Opportunistic Infection of Herpes Simplex Virus Type 1," *Immunology Letters*, vol. 44, pp. 59-66, 1995.
Karpus et al., "Differential CC Chemokine-Induced Enhancement of T Helper Cell Cytokine Production," *Journal of Immunology*, vol. 158 (1997), pp. 4129-4136.
Vicenzi et al., Divergent Regulation of HIV-1 Replication in PBMC of Infected Inviduals by CC Chemokines: Suppression by RANTES, MIP-1β, and MCP-3, and Enhancement by MCP-1, *Journal of Leukocyte Biology*, vol. 68 (2000), pp. 405-412.
Karpus et al., "Monocyte Chemotactic Protein 1 Regulates Oral Tolerance Induction by Inhibition of T Helper Cell 1-Related Cytokines," *The Journal of Experimental Medicine*, vol. 187 (1998), pp. 733-741.
Sozzani et al., "Interleukin 10 Increases CCR5 Expression and HIV Infection in Human Monocytes," *The Journal of Experimental Medicine*, vol. 187 (1998), pp. 439-444.
Gu et al., "Control of $T_H2$ Polarization by the Chemokine Monocyte Chemoattractant Protein-1," *Nature*, vol. 404, pp. 407-411, Mar. 23, 2000.

*Primary Examiner*—Elli Peselev
(74) *Attorney, Agent, or Firm*—Kolisch Hartwell, P.C.

(57) ABSTRACT

The object of the present invention is to provide the use of glycyrrhizin and its derivatives for inhibition of MCP-1 production. The present invention discloses an MCP-1 production inhibition method and pharmaceutical composition for the same comprising administration of glycyrrhizin and its derivatives in an amount effective for said inhibition to mammals in which migration of monocytes or T lymphocytes is increased, or production of IL-10 is increased, and inhibition of said increase is desired.

4 Claims, 4 Drawing Sheets

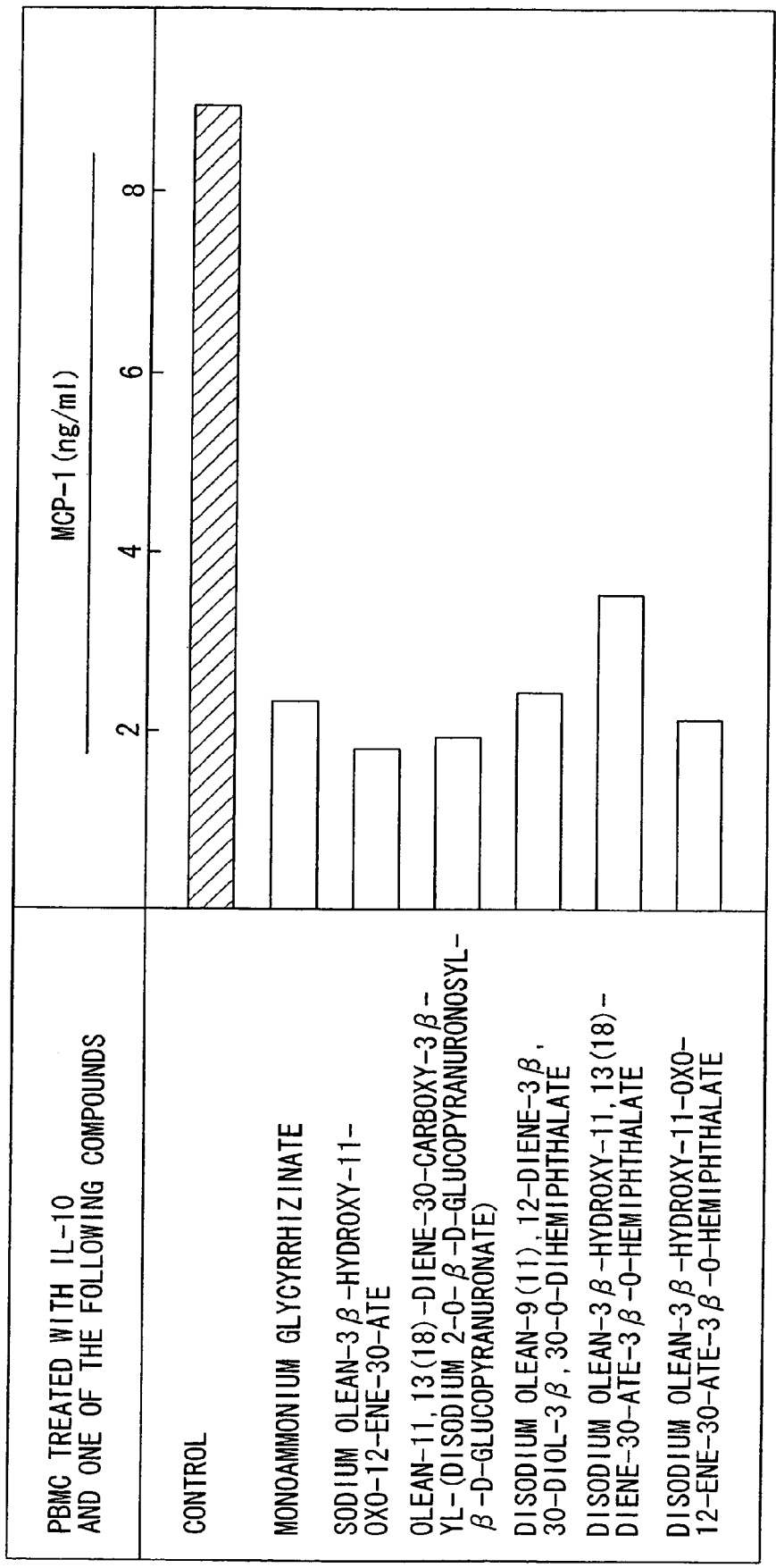

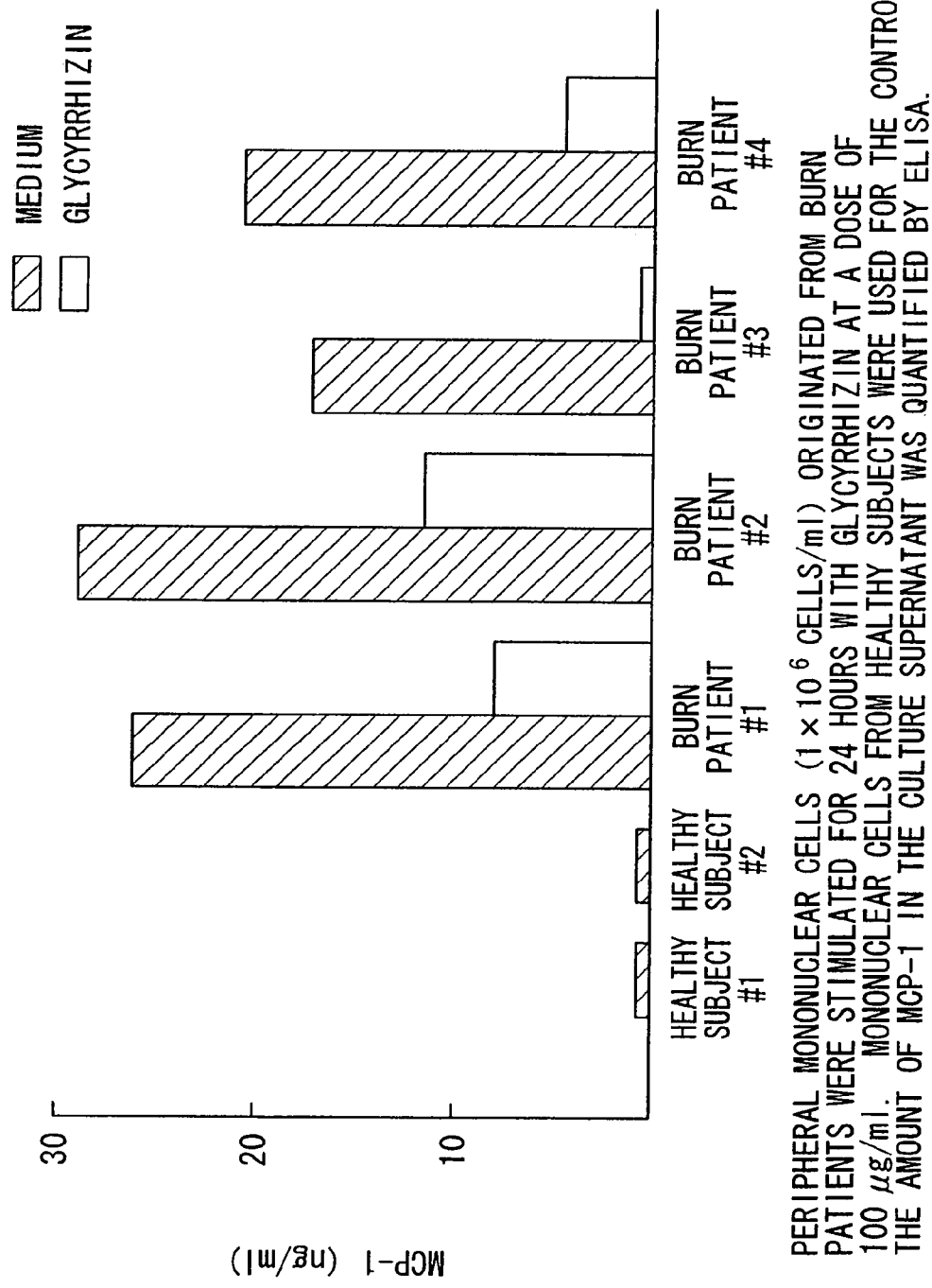

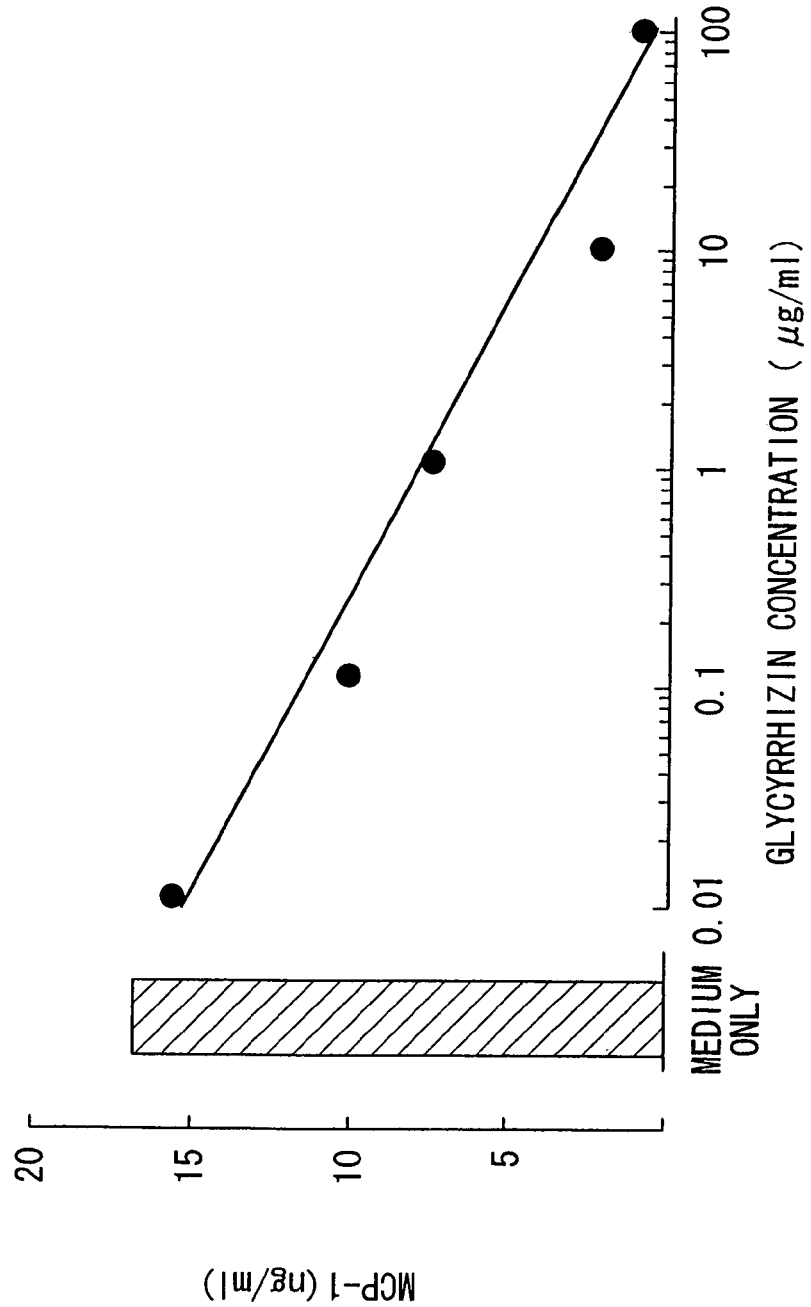

Fig. 4A

EFFECT OF GLYCYRRHIZIN ON DEFENSE AGAINST HERPES SIMPLEX TYPE I INFECTION

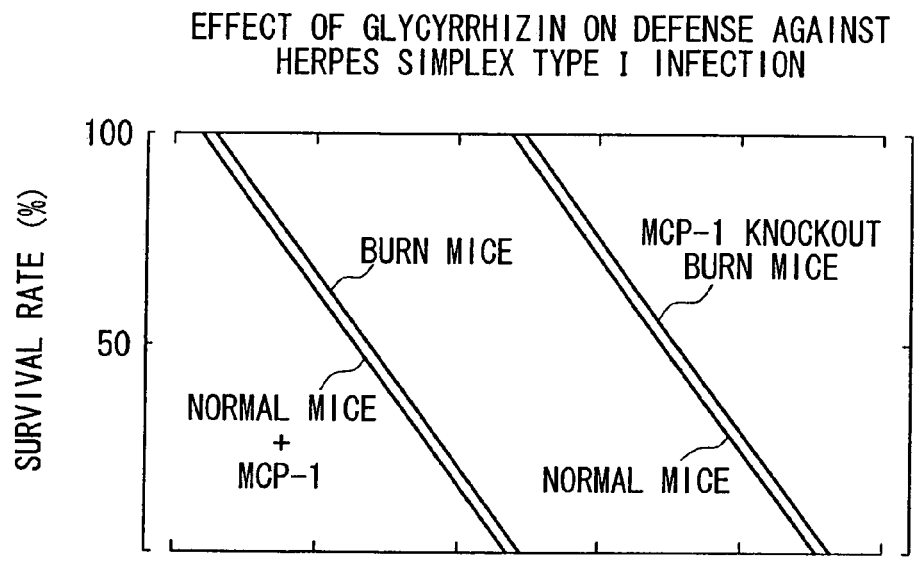

Fig. 4B

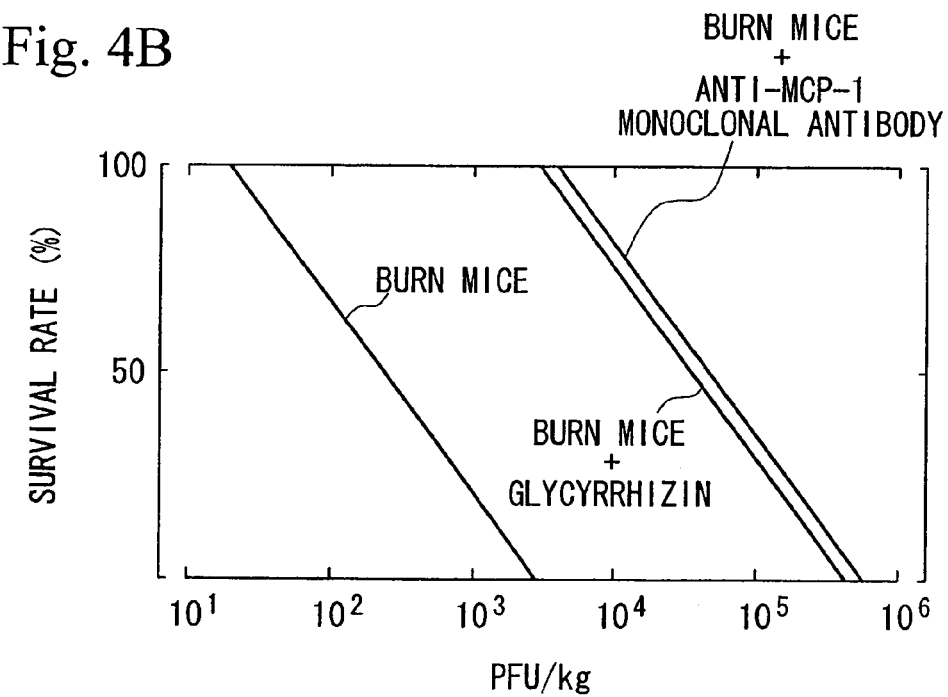

NORMAL MICE, BURN MICE AND MCP-1 KNOCKOUT BURN MICE WERE INTRAPERITONEALLY INFECTED WITH HSV-1 AT $10^1$ TO $10^6$ PFU/kg.
(A) MCP-1 (50 ng/MOUSE) WAS SUBCUTANEOUSLY ADMINISTERED TO NORMAL MICE 2 HOURS BEFORE AND 24 HOURS AFTER INFECTION.
(B) ANTI-MCP-1 MONOCLONAL ANTIBODY (10 μg/MOUSE) WAS SUBCUTANEOUSLY ADMINISTERED TO BURN MICE 2 HOURS BEFORE AND 12 AND 24 HOURS AFTER INFECTION.
GLYCYRRHIZIN (20 mg/kg) WAS ADMINISTERED INTRAPERITONEALLY IMMEDIATELY AFTER AND 2 HOURS AFTER INFECTION. THE SURVIVAL RATE OF EACH GROUP 2 WEEKS AFTER INFECTION ARE SHOWN IN THE GRAPHS.

USE OF GLYCYRRHIZIN AND ITS DERIVATIVES AS MCP-1 PRODUCTION INHIBITORS

CROSS-REFERENCES TO RELATED APPLICATIONS

This application claims the priority benefit of U.S. Provisional Application Ser. No. 60/422,338 filed Oct. 29, 2002.

BACKGROUND OF THE INVENTION

1. Field of the Invention

The present invention relates to the use of glycyrrhizin and its derivatives for inhibition of MCP-1 production and the production of an MCP-1 production inhibitor, a method for inhibiting MCP-1 production, a method for controlling infections through the inhibition of MCP-1 production, and a pharmaceutical composition for the same.

2. Description of the Related Art

<MCP-1 Chemokines>

Cytokines are proteins produced by lymphocytes and other cells, and act on cells having receptors to them to carry out cell growth, differentiation and expression of function. In addition, cytokines also include a group of proteins referred to as chemokines having the action of causing migration of leukocytes. These chemokines have a common structure in which they have four cysteine residues, and are classified into subfamilies such as CXC, CC and so forth according to the motif formed by two cysteine residues on the N terminal side.

Chemokines belonging to the CXC subfamily have a sequence in which the first two cysteine residues on the N terminal side surround one amino acid, namely have CXC, and induce chemotaxis in vitro particularly in neutrophils. On the other hand, chemokines belonging to the CC subfamily differ from those belonging to the CXC subfamily in that they have an amino acid sequence in which the first two cysteine residues on the N terminal side are arranged in a row directly without having an amino acid between them, and are known to induce chemotaxis in vitro in monocytes, macrophages, T cells, NK cells, eosinophils and so forth.

MCP-1 (monocytechemoattractant (chemotactic) protein-1) is a CC chemokine that is a protein composed of 76 amino acids and having a molecular weight of 8,000 to 18,000. When monocytes, macrophages, fibroblasts or vascular endothelial cells and so forth are stimulated by a bacterial infection and the like, MCP-1 is thought to be produced and secreted by these cells and promote local tissue infiltration by macrophages, T cells and so forth at the site of the infection. In addition, MCP-1 has been observed to be independently and constantly produced by certain types of tumor cells.

Infection resistance to various infectious diseases is known to decrease when the type 2 T cell reaction becomes dominant. In MCP-1 knockout mice, type 2 T cells do not appear. In other words, MCP-1 has been demonstrated to be required for establishment of a type 2 T cell reaction. If it were possible to stop the production of MCP-1, an individual would not have to go through a state in which the type 2 T cell reaction is dominant, thereby preventing that individual from succumbing to an infectious disease. For example, in the case the type 2 T cell reaction has become dominant with MCP-1, infection sensitivity increases 100-fold in the case of Herpes infections and 50-fold in the case of Candida infections, thereby resulting in exacerbation of Herpes encephalitis, Cryptococcus encephalitis and pneumonia. In addition, in a state in which the type 2 T cell reaction has become dominant, since the anti-tumor immunity of an individual to tumors is not induced, there is greater susceptibility to accelerated tumor growth and opportunistic infections in individuals with cancer.

Thus, if it were possible to inhibit the action of MCP-1, it is thought that desirable effects would be obtained in these diseases and so forth.

SUMMARY OF THE INVENTION

As a result of earnest studies to achieve the above object, the inventors of the present invention focused on glycyrrhizin (glycyrrhizinic acid) and its derivatives.

Glycyrrhizin (or glycyrrhizinic acid) is a compound composed of glycyrrhetic acid and two molecules of glucuronic acid, and has been known since long ago to have anti-inflammatory action. In addition, it is also known to have gastric juice secretion inhibitory action, digestive organ ulcer healing action, action that enhances antiallergic activity, immunosuppressive activity, liver function enhancing action, detoxifying action and action that enhances resistance to viruses. In particular, it is a compound that is widely used in the clinical setting as a liver disease agent and allergy agent.

Glycyrrhizin has been reported in recent years to have action that inhibits the intracellular growth of HIV, and have an effect that allows survival for 10 years or more without the onset of AIDS when glycyrrhizin is administered at 150 to 225 mg (6 to 9 tablets) per day to patients who are asymptomatic carriers (AC).

The inventors of the present invention found that glycyrrhizin and its derivatives have action that inhibits production of MCP-1, thereby leading to completion of the present invention.

The present invention provides the use of glycyrrhizin and its derivatives for inhibition of MCP-1 production.

The glycyrrhizin and its derivatives used in the present invention are represented with the following general formula (I):

[wherein, $R^1$ represents a hydrogen atom or a group of the following formula (II) or (III):

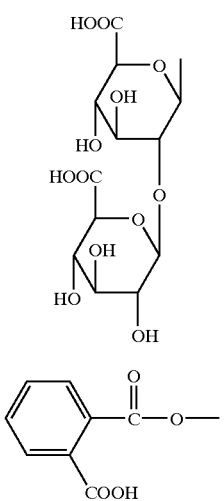

(II)

(III)

or their pharmaceutically acceptable salts);

$R^2$ represents COOH or a group of the following formula (IV):

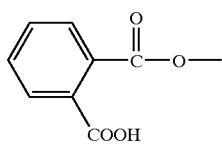

(IV)

or their pharmaceutically acceptable salts;

X represents C=O or CH; and, dotted lines suitably represent a double bond].

In the above compounds, the pharmaceutically acceptable salts in formulas (II), (III) and (IV) are sodium salts, potassium salts, calcium salts, magnesium salts, aluminum salts, ammonium salts or various other organic amine salts, but preferably are sodium salts, potassium salts, ammonium salts or combinations thereof.

The following compounds are included in the above general formula (I):

olean-11,13(18)-diene-30-carboxy-3β-yl-(disodium 2-O-β-glucopyranuronosyl-β-D-glucopyranuronate);

sodium olean-3β-hydroxy-11-oxo-12-ene-30-ate;

disodium olean-9(11),12-diene-3β,30-diol-3β, 30-O-di-hemiphthalate;

disodium olean-11,13(18)-diene-3β,30-diol-3β,30-O-di-hemiphthalate;

disodium olean-3β-hydroxy-11,13(18)-diene-30-ate-3β-O-hemiphthalate;

disodium olean-3β-hydroxy-11-oxo-12-ene-30-ate-3β-O-hemiphthalate; and monoammonium 20β-carboxy-11-oxo-30-norolean-12-en-3β-yl-2-O-β-D-glucopyranuronosyl-β-D-glucopyranosi-douronate.

The present invention also provides an MCP-1 production inhibition method comprising: administration of a compound according to claim 1 or claim 2 in an amount effective for said inhibition to mammals in which migration of monocytes or T lymphocytes is increased, or production of IL-10 is increased, and inhibition of said increase is desired.

Moreover, the present invention provides an infection control method comprising: providing infection resistance to an individual by inhibiting production of MCP-1 to control susceptibility to infection of said individual induced by MCP-1.

In addition, the present invention provides the use of the above glycyrrhizin and its derivatives in the production of an MCP-1 production inhibitor.

Moreover, the present invention provides a pharmaceutical composition for treatment or prevention of decreases in infection resistance to opportunistic infections occurring in burn patients, AIDS patients, cancer patients, encephalitis patients, individuals having suffered serious injuries or undergone major surgery, individuals subject to stress or other individuals in which production of MCP-1 has been induced, comprising:

a compound according to claim 1 or claim 2, along with an arbitrary pharmaceutically acceptable carrier, in an amount effective for treating or preventing decreases in infection resistance to opportunistic infections occurring in said individuals.

BRIEF DESCRIPTION OF THE DRAWINGS

FIG. 1 is a graph showing the effects of glycyrrhizin on MCP-1 production by peripheral blood mononuclear cells stimulated with IL-10.

FIG. 2 is a graph showing the inhibitory effects of glycyrrhizin on MCP-1 production by peripheral blood mononuclear cells from burn patients.

FIG. 3 is a graph showing the inhibitory effects of glycyrrhizin on MCP-1 production by peripheral blood mononuclear cells from AIDS patients.

FIGS. 4A and 4B are drawings showing the effects of administration of glycyrrhizin on increased sensitivity to HSV-1 infection in burn mice.

DETAILED DESCRIPTION OF THE PREFERRED EMBODIMENTS

The glycyrrhizin and its derivatives used for inhibiting the production of MCP-1 in the present invention can be acquired from, for example, Minophagen Pharmaceutical Co., Ltd. Alternatively, glycyrrhizin derivatives are described in, for example, Japanese Unexamined Patent Application, First Publication No. Sho 63-2959; Chem. Pharm. Bull. 34, 897 (1986); and Jpn. J. Pharmacol., 71, 281 (1996).

Disodium olean-3β-hydroxy-11-oxo-12-ene-30-ate-3β-O-hemiphthalate can be synthesized in the manner described below.

Synthesis Method of Disodium Olean-3β-Hydroxy-11-Oxo-12-Ene-30-Ate-3β-O-Hemiphthalate 300 ml of methanol and 30 ml of 1 N aqueous sodium hydroxide solution were added to 10 g of olean-11,13(18)-diene-3-hydroxy-30-ate-3-O-hemiphthalic acid, and stirred to dissolve. Aqueous sodium hydroxide solution was added during stirring so that the pH of the reaction solution stayed within the range of 10.0–10.4. After adjusting the reaction solution, the solution was filtered using a membrane filter. Following filtration, the reaction solution was concentrated to about half of its original volume, 200 ml of acetone were added, and the white crystals that precipitated were recovered and dried. 9.3 g of the above compound, which is one of the compounds used in the present invention, were obtained. The melting point was 283–287° C., and the mass analysis value (m/z) was 601 (M−1).

Synthesis Method of Olean-11,13(18)-Diene-3-Hydroxy-30-Ate-3-O-Hemiphthalic Acid A mixture of 30 g of olean-11,13(18)-diene-3-hydroxy-30 acid, 60 g of phthalic anhydride and 2 g of 4-dimethylaminopyridine were added to 300 ml of chloroform, and refluxed for 24 hours at 80° C. Following completion of the reaction, the solvent was distilled off and 240 ml of ethanol were added to the residue. After dissolving by heating at 90° C., 240 ml of water were added followed by heating and stirring for an additional 15 minutes. After cooling, the precipitated white crystals were recovered, and 200 ml of 50% ethanol were added to these crystals after which heating and stirring were continued for 30 minutes. After cooling, the white crystals that did not dissolve were recovered by filtration, and then washed with 50% aqueous ethanol and dried to obtain 37.6 g of olean-11,13(18)-diene-3-hydroxy-30-ate-3-O-hemiphthalic acid.

Synthesis Method of Olean-11,13(18)-Diene-3-Hydroxy-30 Acid 47.1 g of 18α-glycyrrhetic acid were dissolved in 500 ml of tetrahydrofuran (THF) and then mixed with 500 ml of 1 N aqueous sodium hydroxide solution and 500 ml of THF at 80° C., after which a solution containing 75.6 g of sodium borohydroxide was dropped in to this mixture and allowed to react for 24 hours at the same temperature. Following completion of the reaction, the reaction solution was returned to room temperature followed by the addition of 600 ml of acetone and stirring, and neutralization of the solution using 2 N hydrochloric acid. The THF in the reaction solution was distilled off, and the white crystals that precipitated (mixture of 11α-hydroxy-glycyrrhetic acid and 11β-hydroxy-glycyrrhetic acid) were recovered by filtration. After dissolving these crystals in 1000 ml of THF and drying, the solvent was distilled off and 400 ml of chloroform were added to the residue followed by recovery of the insoluble crystals by filtration and drying to obtain 40 g of a mixture of 11α-hydroxy-glycyrrhetic acid and 11β-hydroxy-glycyrrhetic acid. This mixture was dissolved in 4000 ml of THF followed by the addition of 1600 ml of 10% hydrochloric acid and stirring for 3 hours at room temperature. The white crystals that precipitated were recovered by filtration, washed with water and dried to obtain 35.8 g of olean-11,13(18)-diene-3-hydroxy-30-oic acid.

In addition, the glycyrrhizin and its derivatives used in the present invention can also be obtained from resources that exist in nature such as licorice having glycyrrhizin as one of its components or licorice powder, licorice extract or crude licorice extract obtained from licorice.

Although the present invention provides an MCP-1 production inhibition method comprising the administration of glycyrrhizin and its derivatives in an amount effective for said inhibition to mammals in which migration of monocytes or T lymphocytes is increased, or production of IL-10 is increased, and inhibition of said increase is desired, more specifically, this method can be applied in the case migration of monocytes or T lymphocytes is increased, and inflammation is occurring due to infiltration of monocytes or T lymphocytes.

Infection resistance to various infectious diseases is known to decrease when the type 2 T cell reaction becomes dominant. In MCP-1 knockout mice, type 2 T cells do not appear. In other words, MCP-1 has been demonstrated to be required for establishment of a type 2 T cell reaction. If it were possible to stop the production of MCP-1, an individual would not have to go through a state in which the type 2 T cell reaction is dominant, thereby preventing that individual from succumbing to an infectious disease. For example, in the case the type 2 T cell reaction has become dominant with MCP-1, infection sensitivity increases 100-fold in the case of Herpes infections and 50-fold in the case of Candida infections, thereby resulting in exacerbation of Herpes encephalitis, Cryptococcus encephalitis and pneumonia. In addition, in a state in which the type 2 T cell reaction has become dominant, since the anti-tumor immunity of an individual to tumors is not induced, there is greater susceptibility to accelerated tumor growth and opportunistic infections in individuals with cancer. Thus, the control method of the invention of the present application can be applied to treatment or prevention of decreases in infection resistance to opportunistic infections occurring in burn patients, AIDS patients, cancer patients, encephalitis patients, individuals having suffered serious injuries or undergone major surgery, individuals subject to stress or other individuals in which production of MCP-1 has been induced.

Thus, the present invention also provides an infectious disease control method that provides infection resistance to individuals by controlling susceptibility to infections of said individuals caused by MCP-1 by inhibiting production of MCP-1. In the case the type 2 T cell reaction has become dominant due to MCP-1 resulting in increased susceptibility to infection, this method is useful since it is able to improve this increased susceptibility. Namely, when a type 1 T cell reaction has been activated in the case bacteria and so forth have invaded the body, although the spread of these bacteria throughout the body can be inhibited, when the induction of type 1 T cells or the function of effector cells of the type 1 T cell reaction (macrophages, natural killer cells and cytotoxic T cells) has been inhibited by IL-4 and IL-10 produced by type 2 T cells following induction of a type 2 T cell reaction, the body is unable to extricate the bacteria resulting in exacerbation of the infection. Since MCP-1 induces type 2 T cells, a method that inhibits the production of MCP-1 can be applied in the case it is desired to increase resistance to bacterial infection of an individual. In addition, since type 2 T cells lower the resistance of an individual to infections caused by viruses and molds, it can also be applied in the case of desiring to increase resistance of an individual to viruses and mold infections.

Although diseases of mammals in a state in which the migration of monocytes or T lymphocytes is increased or the production of IL-10 is increased are included in specific application targets of the MCP-1 production inhibition method of the present invention, specific examples of such diseases include inflammations and decreased resistance to infection.

In addition, the MCP-1 production inhibition method of the present invention can also be applied to individuals in which production of MCP-1 has been induced, examples of which include burn patients, AIDS patients, cancer patients, encephalitis patients, individuals having suffered serious injuries or undergone major surgery and individuals subject to stress.

In the MCP-1 production inhibition method of the present invention, glycyrrhizin and its derivatives are preferably used in the form of a pharmaceutical composition of the invention of the present application, namely a form that contains glycyrrhizin and its derivatives in an amount effective for treatment and prevention of the intended target diseases or target states in the present application (or control of the mechanisms of action that cause said diseases or states such as increased migration of monocytes) and an arbitrary pharmaceutically acceptable carrier.

In a pharmaceutical composition of the present invention, glycyrrhizin and its derivatives may be contained alone, or mixed with an arbitrary pharmaceutically acceptable carrier. In addition, a pharmaceutical composition of the present invention can be prepared in various forms in accordance with ordinary methods, examples of said forms include tablets, injections, capsules, sprays, troches and powder.

A "pharmaceutically acceptable carrier" arbitrarily contained in a pharmaceutical composition of the present invention refers to that which does not substantially inhibit the function of the active ingredient in said composition, and more specifically, includes solid diluents or fillers, sterile aqueous solvents and various nontoxic organic solvents.

Although an MCP-1 production inhibitor or pharmaceutical composition for control of increased migration of monocytes obtained according to the invention of the present application can be administered to mammals orally, rectally, locally, percutaneously, intravenously or intramuscularly, the administration route is suitably selected by the clinician depending on the weight and health status of the patient to be treated or prevented as well as the status of the disease to be treated.

In the case of administering an MCP-1 production inhibitor of the invention of the present application, it is normally administered at a dose of 0.1 to 100 mg per day per kg of body weight.

EXAMPLES

Example 1

Inhibitory Effect of Glycyrrhizin and its Derivatives on Production of MCP-1

Experimental Method

Peripheral blood was collected from health individuals and the fraction containing peripheral blood mononuclear cells (PBMC) was isolated with Ficoll-Hypaque.

Monocytes were inoculated into each well of a 96-well flat-bottom microtiter plate at a concentration of $1\times10^6$ cells/ml. RPMI1640 medium containing 10% FCS and antibiotics (penicillin and streptomycin) was used for culturing. The cells were cultured using an incubator maintained at a temperature of 37° C. and $CO_2$ concentration of 5%.

The cells were stimulated by addition of 20 ng/ml of IL-10 (acquired from PeproTech) to each well, and a solution of glycyrrhizin or its derivatives was added at a concentration of 100 µg/ml to all wells except the control well, after which culturing was continued for 24 hours.

Following addition of glycyrrhizin, the culture supernatant was recovered and the amount of MCP-1 in the supernatant was quantified by ELISA. A commercially available kit (trade name: Human MCP-1 BD OptEIA ELISA Kit) was used for ELISA.

Results

The results are shown in FIG. 1. Although production of MCP-1 increased in the samples to which IL-10 was added, glycyrrhizin (monoammonium glycyrrhizinate; monoammonium glycyrrhizinate is described as glycyrrhizin in FIGS. 2 through 4) and its derivatives were determined to have the effect of inhibiting the production of MCP-1 induced by IL-10.

Example 2

Inhibition of MCP-1 from Peripheral Blood Mononuclear Cells from Burn Patients by Glycyrrhizin Experimental Method Peripheral blood was collected from burn patients (third-degree burns covering 45–78% of the body surface), and peripheral blood mononuclear cells were isolated with Ficoll-Hypaque. $1\times10^6$ cells/ml of the peripheral blood mononuclear cells were stimulated for 24 hours with 100 µg/ml of glycyrrhizin. Furthermore, mononuclear cells from healthy subjects were cultured under the same conditions for the control. The amount of MCP-1 in the culture supernatant was measured with the Human MCP-1 BD OptEIA ELISA Kit.

Results

The results are shown in FIG. 2. As is clear from the graph, in contrast to MCP-1 not being produced in the mononuclear cells of healthy subjects, MCP-1 was prominently produced in the mononuclear cells from the burn patients. Glycyrrhizin effectively inhibited the production of MCP-1 by mononuclear cells from burn patients.

Example 3

Inhibition of MCP-1 Production from Peripheral Blood Mononuclear Cells from AIDS Patients by Glycyrrhizin Experimental Method Peripheral blood was collected from AIDS patients and the fraction containing peripheral blood mononuclear cells was isolated using Ficoll-Hypaque. Mononuclear cells were inoculated into each well of a 96-well flat-bottom microtiter plate at a concentration of $1\times10^6$ cells/ml. The medium was the same as that used in Example 1. The cells were cultured using an incubator maintained at a temperature of 37° C. and $CO_2$ concentration of 5%.

Glycyrrhizin solution was added to each well except the control well at a final concentration of 0.1 to 100 µg/ml followed by culturing for 24 hours.

Following addition of glycyrrhizin, the culture supernatant was recovered and the amount of MCP-1 in the supernatant was quantified by ELISA. A commercially available kit (trade name: Human MCP-1 BD OptEIA ELISA Kit) was used for ELISA.

Results

The results are shown in FIG. 3. According to this graph, mononuclear cells from AIDS patients were determined to exhibit increased production of MCP-1. In addition, when glycyrrhizin was added to mononuclear cells from AIDS patients within the range of 0.1 to 100 µg/ml and the cells were cultured, production of MCP-1 was found to be inhibited.

Example 4

Effect of Glycyrrhizin on Herpes Simplex Type I Viral Infection

Experimental Method One day after subjecting normal mice and MCP-1 knockout mice to third degree burns over 15% of their body surface area, the animals were intraperitoneally infected with HSV-1 in an amount of $1\times10^1$ to $1\times10^6$ pfu/kg body weight. For the control, normal mice were infected with HSV-1 under the same conditions. In addition, MCP-1 (50 ng/mouse) was administered subcutaneously to normal mice 2 hours before infection and 12 and 24 hours after infection. Anti-MCP-1 monoclonal antibody (10

μg/mouse) was administered subcutaneously to the burn mice 2 hours before infection and 12 and 24 hours after infection.

Results

The results are shown in FIG. 4. According to these graphs, infection sensitivity to HSV-1 infection in burn mice and MCP-1 dosed mice was found to be 100 times higher as compared with the infection sensitivity of normal mice. On the other hand, in the case of burn mice administered anti-MCP-1 monoclonal antibody and glycyrrhizin, infection sensitivity to HSV-1 infection was determined to recover to the same level as normal mice. In addition, in knockout mice in which production of MCP-1 was blocked, infection sensitivity to HSV-1 was not observed to change as compared with the normal mice.

The group of compounds synthesized in the invention of the present application are as indicated below.

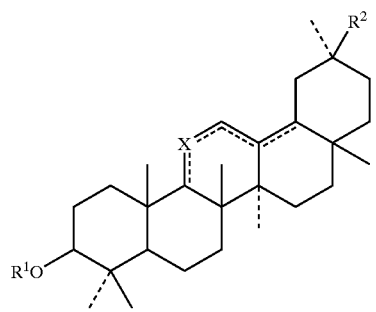
(I)

| Compound No. | Compound Name | X | R¹ | R² |
|---|---|---|---|---|
| MUN-003 | olean-11,13(18)-diene-30-carboxy-3β-yl-(disodium 2-O-β-glucopyranuronosyl-β-D-glucopyranuronate) | CH | NaOOC-(sugar structure with OH, HO, NaOOC, OH, HO, OH) | COOH |
| MUN-011 | sodium olean-3β-hydroxy-11-oxo-12-ene-30-ate | CO | H | COONa |
| MUN-013 | disodium olean-9(11),12-diene-3β,30-diol-3β,30-O-dihemiphthalate | CH | (phthalate structure with COONa) | (phthalate structure with COONa) |
| MUN-014 | disodium olean-11,13(18)-diene-3β,30-diol-3β,30-O-dihemiphthalate | CH | | |
| MUN-016 | disodium olean-3β-hydroxy-11,13(18)-diene-30-ate-3β-O-hemiphthalate | CH | | COONa |
| MUN-018 | disodium olean-3β-hydroxy-11-oxo-12-ene-30-ate-3β-O-hemiphthalate | CO | | |

-continued

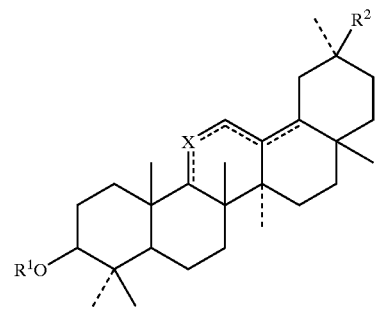

| Compound No. | Compound Name | X | $R^1$ | $R^2$ |
|---|---|---|---|---|
| GR | monoammonium glycyrrhizinate | CO | 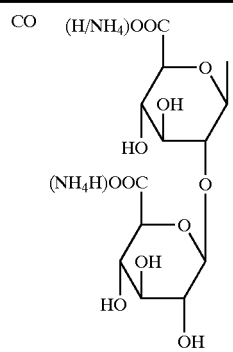 | COOH |

According to the present invention, the production of MCP-1 can be inhibited.

What is claimed is:

1. A method of treating a mammal in which migration of monocytes or T lymphocytes is increased, or production of IL-10 is increased, and inhibition of said increase is desired, comprising: administration of a compound represented by the following general formula (I) for inhibiting MCP-1 production:

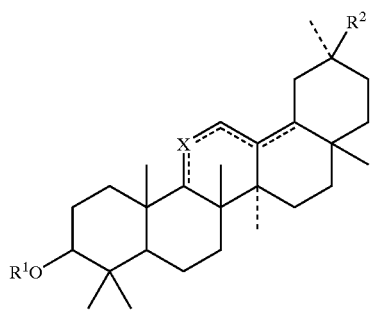

wherein $R^1$ represents a hydrogen atom or a group of the following formula (II) or (III):

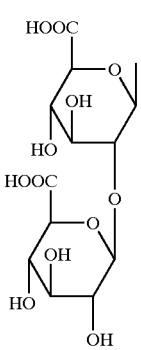

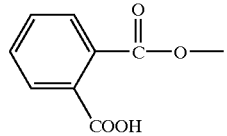

wherein the groups of formula (II) and formula (III) may also be their pharmaceutically acceptable salts;

$R^2$ represents COOH or a group of the following formula (IV):

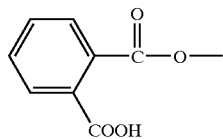 (IV)

or their pharmaceutically acceptable salts;
X represents C=O or CH; and,
dotted lines suitably represent a double bond;
provided that said compound represented by the formula (I) is not MUN-014 or glycyrrhizin (GR).

2. The method according to claim 1 wherein, the pharmaceutically acceptable salts in the above formulas (II), (III) and (IV) are sodium salts, potassium salts, ammonium salts or combinations thereof.

3. The method according to claim 2, wherein the pharmaceutically acceptable salts are sodium salts or ammonium salts.

4. The method according to claim 3 wherein, a compound of the above general formula (I) is one of either:

olean- 11,13(18)-diene-30-carboxy-3β-yl-(disodium 2-O-β-glucopyranuronosyl-β-D-glucopyranuronate);

sodium olean-3β-hydroxy- 11-oxo-12-ene-30-ate;

disodium olean-9(11), 12-diene-3β,30-diol-3 β,30-O-di-hemiphthalate;

disodium olean-3β-hydroxy- 11,13(18)-diene-30-ate-3β-O-hemiphthalate; or disodium olean-3β-hydroxy-11-oxo-12-ene-30-ate-3β-O-hemiphthalate.

* * * * *